(12) United States Patent
Kimura et al.

(10) Patent No.: US 9,895,204 B2
(45) Date of Patent: Feb. 20, 2018

(54) DENTAL HANDPIECE OF CENTER-INJECTION TYPE

(75) Inventors: Takao Kimura, Kanuma (JP); Masanori Mizunuma, Kanuma (JP)

(73) Assignee: Nakanishi Inc., Kanuma-shi (JP)

( * ) Notice: Subject to any disclaimer, the term of this patent is extended or adjusted under 35 U.S.C. 154(b) by 176 days.

(21) Appl. No.: 12/717,763

(22) Filed: Mar. 4, 2010

(65) Prior Publication Data

US 2010/0227293 A1 Sep. 9, 2010

(30) Foreign Application Priority Data

Mar. 6, 2009 (JP) .................................. 2009-054186
Oct. 14, 2009 (JP) .................................. 2009-237172

(51) Int. Cl.
- *A61C 1/10* (2006.01)
- *A61C 1/05* (2006.01)
- *A61C 1/14* (2006.01)

(52) U.S. Cl.
CPC .............. *A61C 1/055* (2013.01); *A61C 1/145* (2013.01)

(58) Field of Classification Search
CPC ........... A61C 1/055; A61C 1/145; A61C 3/02; C08F 214/22; C08F 214/222; C08F 214/225; C08F 214/28
USPC ................... 433/82, 104, 114, 115, 126, 103, 433/116–118, 124, 128, 130, 131
See application file for complete search history.

(56) References Cited

U.S. PATENT DOCUMENTS

| | | | | |
|---|---|---|---|---|
| 2,768,011 A | * | 10/1956 | Mosher | F16J 15/3472 277/399 |
| 3,542,372 A | * | 11/1970 | Edwardson | 277/309 |
| 5,022,857 A | | 6/1991 | Matsutani et al. | |
| 5,096,421 A | | 3/1992 | Seney | |
| 5,676,542 A | * | 10/1997 | Lingenhole | A61C 1/05 433/115 |
| 5,816,803 A | * | 10/1998 | Nakanishi | A61C 1/055 433/115 |
| 2008/0187884 A1 | * | 8/2008 | Boinot | 433/127 |

FOREIGN PATENT DOCUMENTS

| | | |
|---|---|---|
| CA | 2 114 299 A1 | 8/1994 |
| DE | 39 30 114 A1 | 11/1990 |
| EP | 0 497 139 A1 | 8/1992 |
| JP | 8322853 A | 12/1996 |

* cited by examiner

Primary Examiner — Cris L Rodriguez
Assistant Examiner — Mirayda A Aponte
(74) Attorney, Agent, or Firm — Jason D. Voight

(57) ABSTRACT

The dental handpiece of a center-injection type has a bur sleeve (8, 9) having an axial through hole capable of receiving and detachably holding therein a cutting bur having an axial through hole, upper and lower bearings (10, 11) for rotatably supporting the bur sleeve (8, 9), and an injection nozzle (5) capable of being inserted into the axial through hole of the cutting bur from its proximal end for injecting cooling water through the other end. The dental handpiece (1) further has an upper seal means (17) arranged to seal the space between the upper region of the bur sleeve (8, 9) and the upper bearing (10), and a lower seal means (17'9 arranged to seal the space between the lower region of the bur sleeve (8, 9) and the lower bearing (11).

8 Claims, 2 Drawing Sheets

DENTAL HANDPIECE OF CENTER-INJECTION TYPE

This application claims priority of Japanese application number 2009-54186, filed Mar. 6, 2009, and Japanese application number 2009-237172, filed Oct. 14, 2009.

FIELD OF ART

The present invention relates to a dental handpiece of a center-injection type, which injects water through a cutting bur and may be used in dental implant surgery. In particular, the present invention relates to a dental handpiece of a center-injection type which has seal means for preventing intrusion of contaminants into the interior of the head casing of the handpiece.

BACKGROUND ART

A dental handpiece of a center-injection type has hitherto been used mainly for drilling and tapping the jawbone in dental implant surgery. A handpiece of this type is shown in FIG. 2 and disclosed in JP-8-322853-A (U.S. Pat. No. 5,816,803-A), which has bur sleeve 104 arranged vertically in the head casing 125 of the handpiece, and detachably holding therein cutting bur 100 having an axial through hole, such as a drill, for rotation. Water injection nozzle 120 connected to a cooling water feed source is inserted into the through hole from the upper end of the bur 100. The cooling water may be injected onto a cutting site through injection port 103 at the lower end of the bur 100 for drilling and tapping under water injection.

In such a conventional dental handpiece of a center injection type, when the injection port 103 of the bur 100 is pressed to the cutting site and blocked, the cooling water, such as physiological saline, flows up in a reverse direction through small gap 102 between the outer surface of the injection nozzle 120 and the inner surface of the bur 100, and leaks out of the bur 100 into the interior of the head casing. The saline from the injection nozzle 120 may cause rusting of the bearings 116, 116' in the head casing and resulting in impairment of the durability of the handpiece.

In order to remedy such a drawback, packing 130 is provided for sealing a gap between the upper end of the bur 100 and the injection nozzle 120 extending out of the through hole 102 at the upper end, in order to prevent saline blowout through the gap.

However, even the gap between the injection nozzle 120 and the upper end of the bur 100 is sealed with the packing 130 against cooling water backflow, microvibrations generated in the treatment are transmitted through the gap 102 from the injection port 103 at the lower end to the upper end of the bur 100, which causes intrusion of contaminants, such as water, blood, or a drug solution, into the interior of the head housing 111. This results in rusting of upper and lower bearings 116, 116' or gear 115 to significantly impair their durability.

SUMMARY OF THE INVENTION

It is therefore an object of the present invention to provide a dental handpiece of a center-injection type in which intrusion of contaminants into the interior of the head casing, in particular into the upper bearing, is effectively prevented.

It is another object of the present invention to provide a dental handpiece of a center-injection type in which the intrusion of contaminants not only through the upper end of the bur into the upper bearing, but also through the lower end of the head casing into the lower bearing is effectively prevented.

According to the present invention, there is provided a dental handpiece of a center-injection type comprising:

a burr sleeve having an axial through hole capable of receiving and detachably holding therein a cutting bur having an axial through hole, upper and lower bearings for rotatably supporting said bur sleeve, a head casing accommodating said bur sleeve and upper and lower bearings, and an injection nozzle communicating with a cooling water feed source at one end, and capable of being inserted into the axial through hole of the cutting bur from its proximal end for injecting cooling water through the other end, characterized in that said dental handpiece further comprises:

an upper seal means arranged to seal a space between the upper region of the bur sleeve and the upper bearing, and a lower seal means arranged to seal a space between the lower region of the bur sleeve and the lower bearing.

According to a preferred aspect of the present invention, the bur sleeve may have a dual structure comprising an inner sleeve capable of receiving and detachably holding therein the cutting bur for rotation, and an outer sleeve arranged around the inner sleeve. The inner sleeve has in its upper end part flaps capable of opening radially outwardly. The head casing includes a push button having a tapered lower end to be brought, when pressed down, into contact with the flaps for opening the same. The outer sleeve in its upper region has an inner diameter larger than the outer diameter of the tapered lower end of the push button, and extends upwardly beyond the upper end of the inner sleeve.

According to another preferred aspect of the present invention, the lower seal means may be an annular member, and arranged around and press-contacted onto the outer surface of the bur sleeve, in particular the inner sleeve.

According to another preferred aspect of the present invention, the dental handpiece may further include a lower seal support attached to the head casing, and the lower seal is held between the lower seal support and the inner sleeve.

According to another preferred aspect of the present invention, the upper seal means may be an annular member, and arranged around and press-contacted onto the outer surface of the outer sleeve.

According to another preferred aspect of the present invention, the dental handpiece may further include an upper seal support attached to the head casing, and the upper seal means is held between the upper seal support and the outer sleeve.

PREFERRED EMBODIMENTS OF THE INVENTION

The present invention will now be explained with reference to a preferred embodiment taken in conjunction with the attached drawings.

Figure 1:
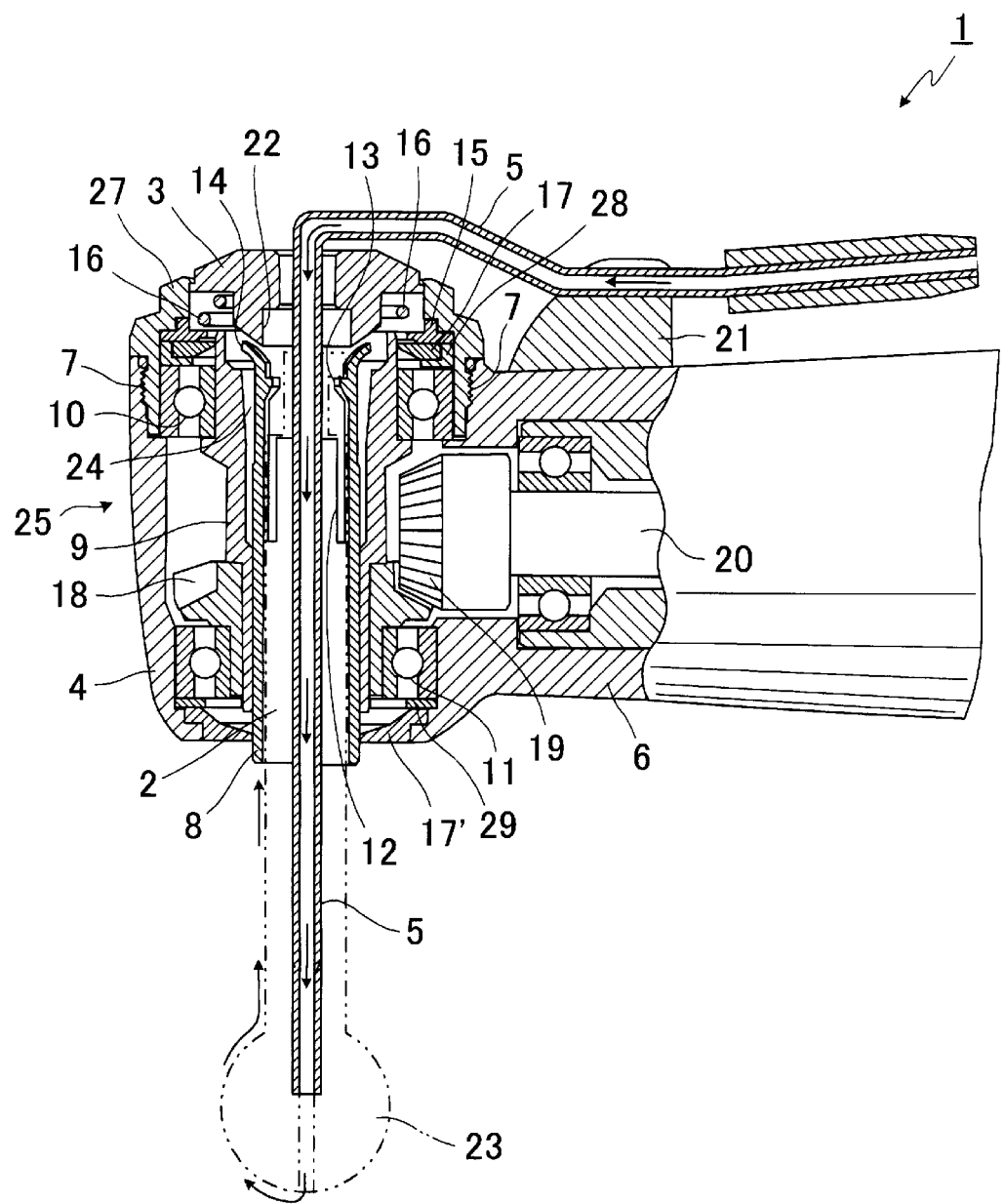
FIG. 1 is a sectional view of the head casing, with various parts inside, of an embodiment of the dental handpiece of a center injection type according to the present invention.
Figure 2:
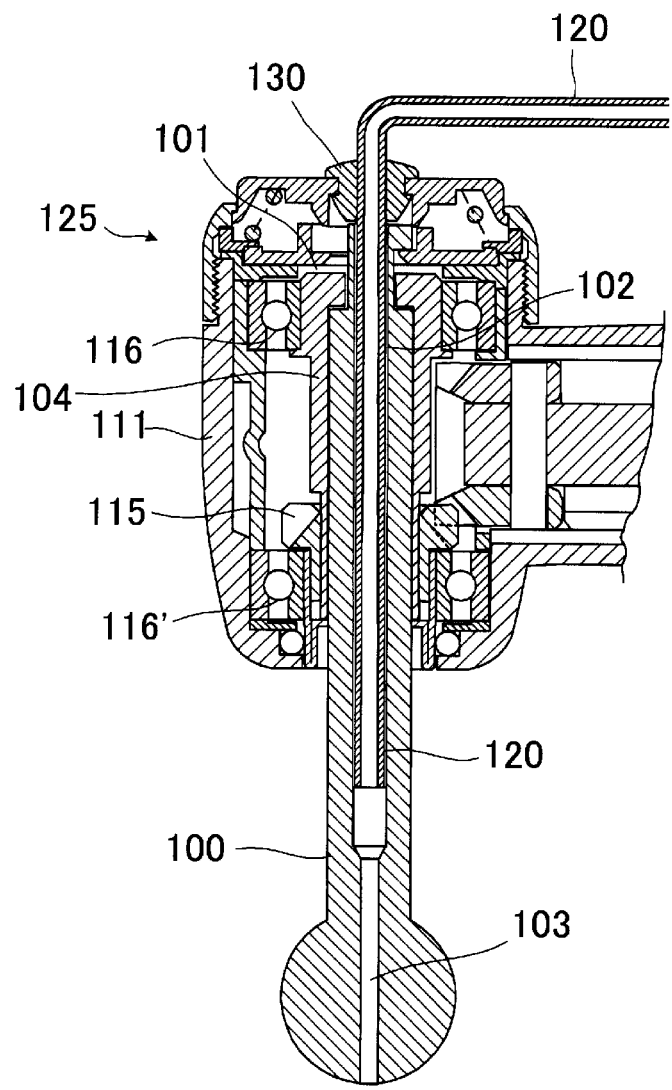
FIG. 2 is a sectional view of the head casing, with various parts inside, of a conventional dental handpiece of a center injection type.

Referring to FIG. 1, dental handpiece 1 of a center injection type is shown, which has head casing 25 provided at the distal end of neck sleeve 6. The head casing 25 accommodates a bur sleeve arranged vertically therein, which is composed of inner sleeve 8 having axial through hole 2 and outer sleeve 9 arranged around the inner sleeve 8. The inner and outer sleeves 8 and 9 are fixed in their lower region by means of an adhesive or welding, and spaced apart in their upper region, forming gap 24 therebetween.

The inner sleeve 8 receives and holds cutting bur 23 in the axial through hole 2. In the upper region of the inner sleeve 8 spaced apart from the outer sleeve 9 with the gap 24, flaps 14 with flared ends are formed by a plurality of slits 12, and each flap 14 is provided with hook 13 for engaging and detachably holding the cutting bur 23 placed in the through hole 2.

The outer sleeve 9 is supported in its upper region by upper bearing 10 disposed in the upper part of the head casing 25, in particular in push button 3 to be discussed later, and in its lower region, via head gear 18, by lower bearing 11 disposed in the lower part of the head housing 4.

The head gear 18 is fixed around the outer sleeve 9 in its lower region, and meshes with bevel gear 19 provided at one end of the drive shaft 20 extending through the neck sleeve 6. The drive shaft 20 is in turn connected to a motor (not shown) at the other end, and rotatably driven by the motor.

The bur sleeve composed by the inner and outer sleeves 8 and 9 fixed together integrally is supported by the upper and lower bearings 10 and 11 located in the upper and lower parts of the head casing 25, respectively, and rotatably driven by the motor via the drive shaft 20, bevel gear 19, and head hear 18. By this driving rotation of the inner and outer sleeves 8 and 9, the cutting bur 23 chucked in the inner sleeve 8 and engaging the hooks 13 is rotated integrally with the bur sleeves 8 and 9.

The head casing 25 includes head housing 4, cap 27 screwed into the top of the head housing 4 via threads 7, and push button 3 arranged in the cap 27. The cap 27 and the push button 3 are assembled so that the push button 3 is actuated upwardly in the cap 27 by means of coil spring 16. The cap 27 has spring support 15 attached inside, and the coil spring 16 is supported between the spring support 15 and the push button 3. The push button 3 has tapered lower end 22, which is arranged facing to the flared end of the flaps 14 of the inner sleeve 8. By pressing the push button 3 down against the thrusting force of the coil spring 16, the tapered lower end 22 pushes the flaps 14 radially outwardly to open, which causes the hooks 13 to be disengaged from the cutting bur 23 to allow the bur 23 to be drawn out of the inner sleeve 8.

Upper seal means 17 is positioned between the upper bearing 10 and the spring support 15 and between the outer sleeve 9 and upper seal support 28 attached inside the cap 27. The upper seal means 17 is a generally annular member made of a sealing material such as fluororubber. The outer periphery of the upper seal means 17 is supported on the upper seal support 28, which limits radially outward movement of the upper seal means 17, and the inner periphery of the upper seal means 17 is in press contact with the outer surface of the outer sleeve 9 near its upper end, so that the upper seal means 17 is held between the upper seal support 28 and the outer sleeve 9. In this manner, the upper seal means 17 is arranged to seal the space between the upper region of the outer bur sleeve 9 and the upper bearing 10, to prevent backflow and intrusion of contaminants through the bur 23, the gap between the bur 23 and the inner sleeve 8, or the gap between the injection nozzle 5 and the bur 23, into the interior of the head casing 25, in particular the upper bearing 10, head gear 18, and bevel gear 19.

Lower seal means 17' is positioned under the lower bearing 11 via lower seal support 29 attached to the head casing 25, between the inner sleeve 8 and the lower end of the head housing 4. The lower seal means 17' is a generally annular member made of a sealing material such as fluororubber. The outer periphery of the lower seal means 17' is supported by the lower seal support 29 and the lower end of the head housing 4, and the inner periphery of the lower seal means 17' is in press contact with the outer surface of the inner sleeve 8, so that the lower seal means 17' is held between the inner sleeve 8 and the lower seal support 29 and the head housing 4. In this manner, the lower seal means 17' is arranged to seal the space between the lower region of the bur sleeve and the lower bearing 11 to prevent intrusion of contaminants from outside the inner sleeve 8 into the interior of the head casing 25, in particular the lower bearing 11, head gear 18, and bevel gear 19.

Injection nozzle 5, which is connected at one end to a cooling water feed source (not shown), is inserted into the through hole of the bur 23 arranged in the through hole 2 of the inner sleeve 8, for injecting water through the other end positioned near the injection port of the bur 23. The injection nozzle 5 is supported on support 21, which is provided on the neck sleeve 6, and has a groove of a U-shaped cross section for receiving and stably supporting the injection nozzle 5 therein.

During treatment, the cutting bur 23 is rotated integrally with the inner and outer sleeves 8 and 9 via gears 18 and 19 and drive shaft 20 by the motor. The rotation of the bur 23 generates vibration, which may cause contaminants at the treatment site to be transferred through the gap between the bur 23 and the inner sleeve 8 into the interior of the head casing 25, in particular up to the area of the upper bearing 10. The intrusion of the contaminants into the upper bearing 10 is securely prevented by the upper seal means 17 arranged between the outer sleeve 9 and the upper seal support 28 for covering the upper face of the upper bearing 10.

The contaminants may also be transferred through another route, i.e. through the gap between the outer surface of the inner sleeve 8 and the inner surface of the head housing 4, into the interior of the head casing 25, in particular into the area of the lower bearing 11. The intrusion of the contaminants into the lower bearing 11 is securely prevented by the lower seal means 17' arranged between the inner sleeve 8 and the lower seal support 29 for covering the lower face of the lower bearing 11.

The dental handpiece of the present invention has an upper seal means arranged to seal the space between the upper region of the bur sleeve and the upper bearing. Even when the cooling water injected through the injection nozzle onto the treatment site, or other contaminants such as blood, flows back through the gap between the cutting bur and the bur sleeve into the interior of the head casing, the intrusion path for the contaminants through the upper end of the bur sleeve into the upper bearing is blocked. Thus, the contaminants are effectively prevented from intruding into the upper bearing by means of the upper seal means.

The dental handpiece of the present invention has a lower seal means arranged to seal the space between the lower region of the bur sleeve and the lower bearing. Even when the contaminants are splashed from the treatment site against the lower end of the head casing, the intrusion path from the cutting side of the bur for the contaminants through the lower end of the head casing into the lower bearing is blocked. Thus, the contaminants are effectively prevented from intruding into the lower bearing by means of the lower seal means.

Accordingly, the interior of the head casing of the handpiece may be prevented from contamination with pathogenic bacteria or biologically hazardous material, such as blood. By preventing intrusion of contaminants into the head casing, rusting of the bearings, gears, and the like in the head casing may be prevented, and the durability of the handpiece is improved.

By making the bur sleeve in a dual structure of which outer sleeve has the upper end having an inner diameter larger than the outer diameter of the tapered lower end of the push button, and extending upwardly beyond the upper end of the inner sleeve, the outer sleeve, to the outer surface of which the upper seal means is press-contacted for sealing, is independent of the push button being pressed down. Thus, the upper seal means may be provided without requiring enlargement of the head casing compared to the conventional size, so that the operability of the handpiece during treatment is not impaired.

Although the present invention has been described with reference to the preferred embodiment, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece (1) of a center-injection type, comprising:
   a bur sleeve (8, 9) having an axial through hole capable of receiving and detachably holding therein a cutting bur having an axial through hole,
   upper and lower bearings (10, 11) for rotatably supporting said bur sleeve (8, 9),
   a head casing (25) accommodating said bur sleeve (8, 9) and upper and lower bearings (10, 11), and
   an injection nozzle (5) communicating with a cooling water feed source at one end, and capable of being inserted into a proximal end of the axial through hole of the cutting bur for injecting cooling water through the other end,
   wherein said dental handpiece further comprises:
   an upper seal (17) in a form of an annular member having an inner periphery and an outer periphery, and arranged around the bur sleeve (8, 9) with said inner periphery press-contacted onto and sealing against an outer surface of said bur sleeve (8, 9) and with said outer periphery supported on the head casing (25) above the upper bearing (10), so that the upper seal (17) is stationary with respect to the head casing (25), and the bur sleeve (8, 9) is rotatable relative to the upper seal (17), so as to seal a space between the upper region of the bur sleeve (8, 9) and an upper region of the head casing (25) and to cover an upper face of the upper bearing (10), and
   a lower seal (17') in a form of an annular member having an inner periphery and an outer periphery, and arranged around the bur sleeve (8, 9) with said inner periphery press-contacted onto and sealing against the outer surface of said bur sleeve (8, 9) and with said outer periphery supported on the head casing (25) below the lower bearing (11), so that the lower seal (17') is stationary with respect to the head casing (25), and the bur sleeve (8, 9) is rotatable relative to the lower seal (17'), so as to seal a space between the lower region of the bur sleeve (8, 9) and a lower region of the head casing (25) and to cover a lower face of the lower bearing (11),
   wherein said bur sleeve has a dual structure comprising an inner sleeve (8) capable of receiving and detachably holding therein the cutting bur for rotation, and an outer sleeve (9) arranged around said inner sleeve (8),
   wherein said inner sleeve (8) has in its upper end part flaps capable of opening radially outwardly,
   wherein said head casing (25) comprises a push button (3) having a tapered lower end (22) to be brought, when pressed down, into contact with said flaps (14) for opening said flaps, and
   wherein said outer sleeve in its upper region has an inner diameter larger than an outer diameter of said tapered lower end of said push button, and extends upwardly beyond the upper end of said inner sleeve.

2. The dental handpiece according to claim 1, further comprising a lower seal support (29) attached to the head casing (25), wherein said lower seal (17') is held between said lower seal support (29) and said inner sleeve (8).

3. The dental handpiece according to claim 1, further comprising an upper seal support (28) attached to the head casing (25), wherein said upper seal (17) is held between said upper seal support (28) and said outer sleeve (9).

4. The dental handpiece according to claim 1, wherein said upper seal (17) is made of a sealing material.

5. The dental handpiece according to claim 1, wherein said lower seal (17') is made of a sealing material.

6. The dental handpiece according to claim 1, wherein the inner and outer sleeves (8,9) are fixed together in their lower region, and spaced apart in their upper region, forming a gap (24) therebetween.

7. The dental handpiece according to claim 1, further comprising an upper seal support (28) attached to the head casing (25), wherein said upper seal (17) is held between said upper seal support (28) and said bur sleeve (8, 9).

8. The dental handpiece according to claim 1, further comprising a lower seal support (29) attached to the head casing (25), wherein said lower seal (17') is held between said lower seal support (29) and said bur sleeve (8, 9).

* * * * *